United States Patent
Ueda et al.

(10) Patent No.: US 6,372,474 B1
(45) Date of Patent: Apr. 16, 2002

(54) CYCLIC LIPOPEPTIDE ACYLASE

(75) Inventors: Satoshi Ueda, Aichi; Miho Tanaka, Tsuchiura; Masami Ezaki, Tsukuba; Kazutoshi Sakamoto, Tsuchiura; Seiji Hashimoto, Tsukuba; Nobutaka Oohata; Masaru Tsuboi, both of Inazawa; Michio Yamashita, Tsukuba, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/659,335

(22) Filed: Sep. 12, 2000

Related U.S. Application Data

(62) Division of application No. 09/147,352, filed as application No. PCT/JP97/02003 on Jun. 11, 1997, now Pat. No. 6,146,872.

(30) Foreign Application Priority Data

Jun. 13, 1996 (JP) .............................................. 8/151948

(51) Int. Cl.⁷ .............................. C12N 9/50; C12P 21/06
(52) U.S. Cl. ...................... 435/231; 435/68.1; 435/212; 435/228; 514/9; 514/11; 530/317; 530/318
(58) Field of Search ................................. 435/231, 212, 435/228, 68.1; 530/317, 318; 514/9, 11

(56) References Cited

U.S. PATENT DOCUMENTS

| | | | |
|---|---|---|---|
| 5,376,634 A | 12/1994 | Uwamoto et al. | 514/9 |
| H1638 H | 3/1997 | Furuta et al. | 514/11 |
| 5,618,787 A | 4/1997 | Jamison et al. | 530/317 |
| 5,629,289 A | 5/1997 | Rodriguez | 530/318 |
| 6,146,872 A * | 11/2000 | Ueda et al. | 435/231 |

OTHER PUBLICATIONS

Computer Derwent Dgene Abstract 1997P–W45450 Peptide WO 9732975 New Cyclic Lipo:Peptide Acylase.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

The present invention provides a cyclic lipopeptide acrylase which may effectively deacylate the acyl side chain of a cyclic lipopeptide compound, specifically FR901379 Substance or its analog thereof shown by the following general formula [I], and a process for production of a cyclic peptide compound which comprises the use of said acylase.

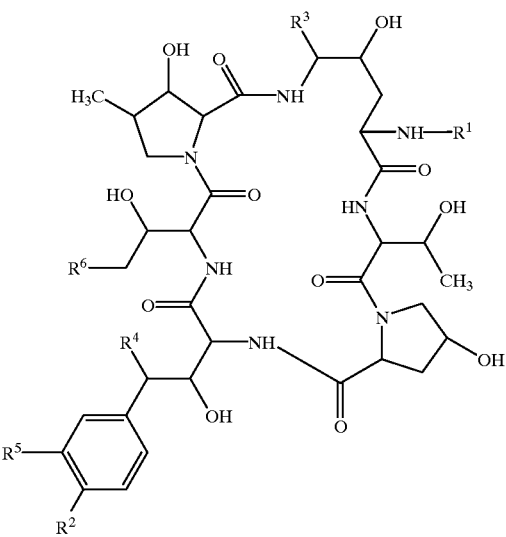

[wherein
$R^1$ is acyl;
$R^2$ is hydroxy or acyloxy;
$R^3$ is hydrogen or hydroxy;
$R^4$ is hydrogen or hydroxy;
$R^5$ is hydrogen or hydroxysulfonyloxy; and
$R^6$ is hydrogen or carbamoyl]

14 Claims, No Drawings

CYCLIC LIPOPEPTIDE ACYLASE

This application is a Division of application Ser. No. 09/147,352 filed on Dec. 31, 1998, now allowed as U.S. Pat. No. 6,146,872, which was originally filed as International Application Number PCT/JP97/02003 on Jun. 11, 1997.

TECHNICAL FIELD

This invention is concerned with an enzyme technology.

The present invention relates to a novel acylase which deacylates the acyl side chain of a cyclic lipopeptide compound and to a deacylation process comprising the use thereof.

More particularly, this invention relates to a novel acylase which deacylates the acyl side chain of FR901379 Substance, which is produced by Coleophoma sp. F-11899 (FERM BP-2635) (as described in Japanese Kokai Tokkyo Koho H3-184921), or any analog of FR901379 Substance and to a deacylation process using the same.

BACKGROUND ART

There has been a standing demand for an acylase capable of deacylating the acyl side chain of a cyclic lipopeptide compound, specifically said FR901379 Substance or an analog thereof, with good efficiency.

DISCLOSURE OF THE INVENTION

The inventors of this invention explored in earnest for a new acylase which might be able to deacylate the acyl side chain of a cyclic lipopeptide compound represented by FR901379 Substance, Echinocandin B and Aculeacin A, the latter two being analogs of FR901379 Substance. As a result, they discovered an acylase in the fermentation broth available upon culture of a certain filamentous fungus and succeeded in achieving the objective deacylation with effectiveness.

The characteristics of the above novel cyclic lipopeptide acylase and of the deacylation process using the enzyme are now described in detail.

The cyclic lipopeptide acylase-producing strain of the invention is first described. The filamentous fungus as a novel cyclic lipopeptide acylase producer specifically includes but is not limited to Oidiodendron sp. No. 30084, *Oidiodendron echinulatum* IFO 31963, *Oidiodendron tenuissimum* IFO 6798, *Oidiodendron truncatum* IFO 9951 and *Oidiodendron truncatum* IFO 31812, all of which belong to the genus Oidiodendron, and Verticillium sp. No. 30085 which belongs to the genus Verticillium.

The mycological characteristics of Oidiodendron sp. No. 30084 and Verticillium sp. No. 30085 are described below.

The fungus strain No. 30084 was isolated from a soil sample collected in Jouhoku-machi, Higashi Ibaraki-gun, Ibaraki Prefecture. This strain grew repressively on various media, forming colonies varying in color, e.g. greenish gray, brownish orange, yellowish white, etc., according to different kinds of culture media. On several media, strain No. 30084 formed anamorphs showing a conidial structure consisting of a dendritic conidiophore rising up from the surface of the medium and arthroconidia formed at its branches.

The detailed mycological characteristics of strain No. 30084 are as follows.

The cultural characteristics of this fungus on various agar media are summarized in Table 1. Colonies on malt extract agar grew repressively and spread to attain diameters from 1.5 to 2.0 cm after 2 weeks of incubation at 25° C. The colony was circular and either raised as a whole or elevated peripherally and depressed in the center. The strain formed anamorphs in abundance, which presented with a powdery surface. The colony was greenish gray with a yellowish gray peripheral zone. The reverse side was light yellow with a yellowish white peripheral zone. On potato dextrose agar, too, the colony grew repressively and spread to attain diameters from 1.5 to 2.0 cm under the same cultural conditions as above. The surface of the colony was centrally elevated or convex, wrinkled, and somewhat felt-like, forming a small amount of anamorphs. The colony was brownish orange to light brown with an orange white peripheral zone. The reverse side was brown with an orange white peripheral zone.

The morphological characteristics of the strain was recorded by observing its growth on Miura's medium (Miura, H. and M. Kudo: Trans. Mycol. Soc. Japan, 11: 116–118; 1970). The conidiophore of strain No. 30084 stood erect from the surface of the medium and consisted of a tan-colored linear trunk and colorless intricate branches. This dendritic structure made the conidiophore clearly distinguishable from the vegetative hypha. The conidiophore was 90 to 220 (or 240) $\mu$m in height, with its trunk being 2 to 3 (or 3.5) $\mu$m wide. The branches were bifurcated or trifurcated in succession and spread to occupy the space 30 to 50 $\mu$m in height and 40–60 $\mu$m in width over top of the conidiophore. Each branch was fragmented along a plurality of septae, forming conidia each in the form of a rod or an ellipsoid truncated at one end or both ends. The conidium was colorless, smooth-surfaced, unicellular, and varied in size from 2–4×1.5–2 $\mu$m. Individual conidia were linked through vestiges of cell walls of the branch. The vegetative hypha was smooth-surfaced, septate, colorless, and branched. The hyphal cell was cylindrical and 1.0–2.5 $\mu$m in width. No clamydospore was observed.

Strain No. 30084 was able to grow at 3 to 32° C. and the optimum temperature for growth was 24 to 28° C. Those data were generated on potato dextrose agar "Nissui" (Nissui Pharmaceutical).

The foregoing characteristics of strain No. 30084 were compared with the descriptions in the taxonomic reference books on fungi such as (G. R. Barron: The Genera of Hyphomycetes from Soil, pp. 239–241, Williams & Wilkins, Baltimore, 1968), (J. A. von Arx: The Genera of Fungi, Sporulating in Pure Culture, pp. 180–184, J. Cramer, Vaduz, 1974) and (K. H. Domsch, W. Gams & T. H. Anderson: Compendium of Soil Fungi, pp. 517–524, Academic Press, London 1980). As a result, the above characteristics were found to agree with the descriptions of the genus Oidiodendron (Oidiodendron Robak 1932). Therefore, the strain was identified to be a strain belonging to the genus Oidiodendron and named Oidiodendron sp. No. 30084.

TABLE 1

Cultural Characteristics of Strain No. 30084

| Medium | Cultural Characteristics |
| --- | --- |
| Malt extract agar* | Growth: repressible, diameters 1.5–2.0 cm. Surface: circular, elevated to centrally concave, powdery, abundant anamorphs. Colonies are greenish gray (1B2–1C2) with yellowish gray (4B2) peripheral zone. |

TABLE 1-continued

Cultural Characteristics of Strain No. 30084

| Medium | Cultural Characteristics |
|---|---|
| | Reverse: pale yellow (4A3) with a yellowish white (4A2) peripheral zone. |
| Potato dextrose agar (Difco 0013) | Growth: repressible, diameters 1.5~2.0 cm. Surface: circular, elevated to centrally convex, wrinkled, slightly felt-like, scanty anamorphs. Brownish orange (6C3) to light brown (6D6) with an orangish white (6A2) peripheral zone. Reverse: brown (7E6) with an orangish white (6A2) peripheral zone |
| Czapek's solution agar* | Growth: very repressible, diameters 0.5~1.0 cm. Surface: circular to amorphous, flat, powdery, abundant anamorphs. Greenish gray (29C2) with a light gray (1B1) peripheral zone. Reverse: Light gray (1B1) to greenish gray (25D2). |
| Sabouraud's dextrose agar medium (Difco 0190) | Growth: repressible, diameters 1.5~2.0 cm. Surface: circular, elevated to centrally convex, slightly felt-like, wrinkled. No anamorph formed. Grayish orange (6B3) to brownish orange (6C7) with an orangish white (6A2) peripheral zone. Reverse: light brown (6D6), with an orangish white (5A2) peripheral zone. |
| Emerson YpSs diameters agar medium (Difco 0739) | Growth: very repressible, 0.5~1.0 cm. Surface: circular, flat, no rise-up of aerial hypha. No anamorph formed. Yellowish white (4A2) Reverse: Yellowish white (4A2) |
| Corn meal agar diameters (Difco 0386) | Growth: very repressible, 1.0~1.5 cm. Surface: circular, flat, no rise-up of aerial hypha. Scanty anamorphs. White (1A1) to yellowish white (4A2) Reverse: yellowish white (4A2) |
| MY20 agar* | Growth: very repressible, diameters 1.0~1.5 cm. Surface: circular, elevated to convex, powdery, wrinkled. Abundant anamorphs. Greenish gray (27D2) in center, with a light gray (1B1) peripheral zone. Reverse: yellowish white (4A2) to pale yellow (4A3). |

*The compositions of malt extract agar, Czapek's solution agar, and MY20 agar are based on JCM Catalog (Nakase, T., 5th ed., 503 p., Japan Collection of Microorganisms and Life Science Research Information Section of the Institute of Physical and Chemical Research, Saitama, 1992).

The above data are the results of observation after 14 days of incubation at 25° C. The color descriptions are based on Methuen Handbook of Colour (Kornerup, A. and J. H. Wanscher, 3rd ed., 525 pp., Methuen, London, 1978).

This strain was originally deposited with National Institute of Bioscience and Human Technology (NIBH, Higashi 1-1-3, Tsukuba-shi, Ibaraki, Japan) (Zip code 305) and assigned with an accession number of FERM P-15550 (date of acceptance: Apr. 2, 1996) but has been converted to a deposit under Budapest Treaty on May 15, 1997 and assigned with an accession number of FERM BP-5943.

The fungus strain No. 30085 was isolated from a soil sample collected in Jouhoku-machi, Higashi Ibaraki-gun, Ibaraki Prefecture. This strain grew repressively on various media, forming colonies varying in color, (e.g. greenish grey, yellowing gray, brown, etc.) and, on several media, produced brown soluble pigments diffusing into the medium. No sporogenic organ was observed normally, but only after prolonged incubation on corn meal agar "Nissui" (Nissui Pharmaceutical), this strain formed a minimal quantity of asexual spores.

The mycological characteristics of strain No. 30085 are as follows.

The cultural characteristics of the strain on various agar media are summarized in Table 2. The colony on potato dextrose agar grew repressively and spread to attain diameters from 2.0 to 3.0 cm after 2 weeks of incubation at 25° C. The colony was circular, flat to elevated, slightly wrinkled and felt-like. An orange-colored exudate was observed on the surface of the colony. The colony was greenish grey to pale gray, with an orangish white to orangish gray peripheral zone. The reverse side was grayish brown to dark brown with a grayish orange peripheral zone and a diffusion of brown soluble pigments into the medium was observed. The colony was Czapek's solution agar grew much repressively and spread circularly to attain diameters of 1.0~2.0 cm after 2 weeks of incubation at 25° C. The surface of the colony was flat and thin, with no rise-up of aerial hyphae. The surface color was white or yellowish gray, and the reverse color was the same.

The morphologic characteristics of strain No. 30085 were determined according to the findings on said corn meal agar "Nissui". The conidiophore of strain No. 30085 was not clearly distinguishable from the vegetative and aerial hyphae, and 2~5 conidiogenous cells occurred in whirl, or at times singly, at the side of the filament. The conidiogenous cell was colorless, smooths-surfaced, filamentous to elongated flask-shaped (lecythiform), measuring 18 to 37 (45 at times)×1.5 to 2 $\mu$m and forming a single conidium to several conidia in a continuous series at the tip. The mode of conidiogenesis appeared to be phialidic but no definite collarette was observed. The conidium was colorless, smooth-surfaced, prolate (ellipsoidal) to bacilliform (rod-shaped), unicellular and 3~5.5×1.5~2.5 $\mu$m in size. The vegetative hypha was smooth-surfaced, septate, colorless and branched, and although it was usually linear but at times curved and remarkably crimped. The hyphal cell was cylindrical to filiform and 1.0~5.0 $\mu$m in width, containing a large number of intracellular vacuoles. Those vacuoles were released extracellularly with aging of the cell to give a highly viscous exudate. The clamydospore, sclerotium and catenulate form (concatinations) were not observed, but in old culture, the pleurogenesis of a large number of globose cells was at times observed.

Strain No. 30085 was able to grow at 4~29° C., and the optimum temperature for growth was 22~26° C. Those data were generated on potato dextrose agar (Nissui pharmaceutical).

The above characteristics of the strain were compared with the descriptions in several books on the taxonomy of fungi, such as (G. R. Barron: The Genera of Hyphomycetes from Soil, pp. 364, Williams & Wilkins, Baltimore, 1968), (J. A. von Arx: The Genera of Fungi, Sporulating in Pure Culture. pp. 315, J. Cramer, Vaduz, 1974) and (K. H.

Domsch, W. Gams & T. H. Anderson: Compendium of Soil Fungi, pp. 859, Academic Press, London, 1980). As a result, strain No. 30085 was found to resemble Verticillium which is a fungus imperfecti (Verticillium Nees 1816). Fungi of the genus Verticillium are different from strain No. 30085 in that the former produce a large number of conidia as a mucoid mass at the tip of the phialide. Regarding this difference, it was considered that strain No. 30085 was able to form only one or a few conidia because of its poor sporogenous ability. Based on the above observation, the strain as identified as a species of the genus Verticillium and named Verticillium sp. No. 30085.

TABLE 2

Cultural characteristics of Strain No. 30085

| Medium | Cultural characteristics |
| --- | --- |
| Malt extract agar* | Growth: repressible, diameters 2.0~3.0 cm. Surface: circular, flat, felt-like to cottony. A pale orange exudate is produced. The colony is pale gray (1B1) to light gray (1C1)-greenish gray (27F2), with an orangish white (5A2) peripheral zone. Reverse: dark green (28F to 4) with a yellowish white (4A2) peripheral zone. |
| Potato dextrose agar (Difco 0013) | Growth: repressible, diameters 2.0~3.0 cm. Surface: circular, flat to elevated, slightly wrinkled, felt-like; an orange-colored exudate produced. Greenish gray (1B2) to pale gray (1B1) with an orangish white (6A2)-orangish gray (6B2) peripheral zone. Reverse: grayish brown (6F3) to dark brown (6F4 to 5), with a grayish orange (5B3)-brown peripheral zone. Diffusion of brown soluble pigments was observed. |
| Czapek's solution agar* | Growth: very repressible, diameters 1.0~2.0 cm. Surface: circular, flat, thin, no rise-up of aerial hyphae, white (1A1) or yellowish gray (2C2) Reverse: white (1A1) or yellowish gray (2C2) |
| Sabouraud's dextrose agar medium (Difco 0190) | Growth: repressible, diameters 2.0~2.5 cm. Surface: circular, elevated to centrally convex; the surface wetted by an exudate and glossy; somewhat wrinkled, and the aerial hyphae in the center were consolidated into a bundle. Yellowish gray (4B2) to grayish yellow (4B3) but light brown (6D4) in the center. Reverse: dark brown (7F6–7) with a brown (7E7) peripheral zone, with diffusion of brown soluble pigments |
| Emerson YpSs agar medium (Difco 0739) | Growth: repressible, diameters 1.5~2.5 cm. Surface: circular, flat to elevated, wrinkled, felt-like, gray with an olive tinge (2E2). Pale gray (2B2) in the peripheral zone. Reverse: dark brown (7F5–6) with a brown (7E5) peripheral zone. Diffusion of brown soluble pigments noted. |

TABLE 2-continued

Cultural characteristics of Strain No. 30085

| Medium | Cultural characteristics |
| --- | --- |
| Corn meal agar (Difco 0386) | Growth: slightly repressible, diameters 2.5~3.0 cm. Surface: circular, flat and thin, with no rise-up at aerial hyphae. Greenish gray (1B2–1C2) but olive (1F3) in the center. Reverse: greenish gray (1C2) but olive (1F3) in the center. |
| MY20 agar* | Growth: much repressible, diameters 0.5~1.0 cm. Surface: circular, elevated to convex, wetted by an exudate and glossy. The aerial hyphae in the center were consolidated into a bundle. Brown (6E4). Reverse: dark brown (6F5), with diffusion of brown soluble pigments. |

The compositions of malt extract agar, Czapek's solution agar, and MY20 agar are based on JCM Catalog Nakase, T., 5th ed., 603 p., Japan Collection of Microorganisms and Life Science Research Information Section of the Institute of Physical and Chemical Research, Saitama, 1992).

Those data were generated by observation after 14 days of incubation at 25° C. after inoculation. The color descriptions are based on Methuen Handbook of Colour (Kornerup, A. and J. H. Wanscher, 3rd ed., 525 pp., Methuen, London, 1978).

This strain was originally deposited with National Institute of Bioscience and Human Technology (NIBH, Higashi 1-1-3, Tsukuba-shi, Ibaraki, Japan) (Zip code 305) and assigned with an accession number of FERM P-15551 (date of acceptance: Apr. 2, 1996). It was initially designated as Fungus No. 30085. However, the strain was renamed Verticillium sp. No. 30085 on Aug. 16, 1996 and converted to a deposit under Budapest Treaty on May 15, 1997 with assignment of an accession number of FERM BP-5944.

Oidiodendron echinulatum IFO 31963, Oidiodendron tenuissimum IFO 6798, Oidiodendron truncatum IFO 9951 and Oidiodendron truncatum IFO 31812 are subcultures allotted from Institute for Fermentation, Osaka (2-17-85 Juso Hommachi, Yodogawa-ku, Osaka-shi).

The term "cyclic lipopeptide compound" as used throughout this specification means a compound having a polypeptide ring and, as a side chain located on the ring, an "acylamino group", which substance optionally may have other side chains.

FR901379 Substance, which is a representative species of said "cyclic lipopeptide compound", is a known compound having antifungal activity as produced by the microorganism Coleophoma sp. F-11899 (FERM BP-2635) (as described in Japanese Kokai Tokkyo Koho H3-184921). It is a compound of the following chemical formula [Ia]:

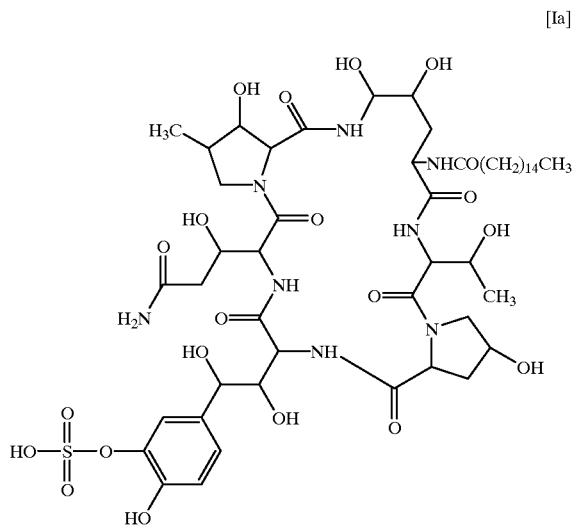

[Ia]

The term "analog of FR901379 Substance" means any compound of the following general formula [I] or a salt thereof.

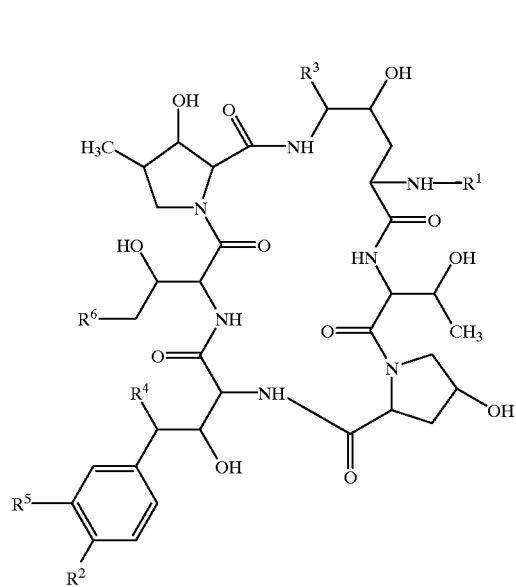

[I]

[wherein
R¹ is acyl;
R² is hydroxy or acyloxy;
R³ is hydrogen or hydroxy;
R⁴ is hydrogen or hydroxy;
R⁵ is hydrogen or hydroxysulfonyloxy; and
R⁶ is hydrogen or carbamoyl]

The novel cyclic lipopeptide acylase according to this invention is an acylase derived from a strain belonging to the genus Oidiodendron or the genus Verticillium and capable of deacylating the side chain "acylamino" group of said cyclic lipopeptide compound to an "amino" group. To be specific, said acylase is an enzyme which deacylates the palmitoyl side chain of FR901379 Substance or a salt thereof or the acyl side chain of the analog of FR901379 Substance of general formula [I], inclusive of FR901379 Substance, or a salt thereof to give the objective cyclic peptide compound, specifically a compound of the following chemical formula [IIa] (FR179642 Substance):

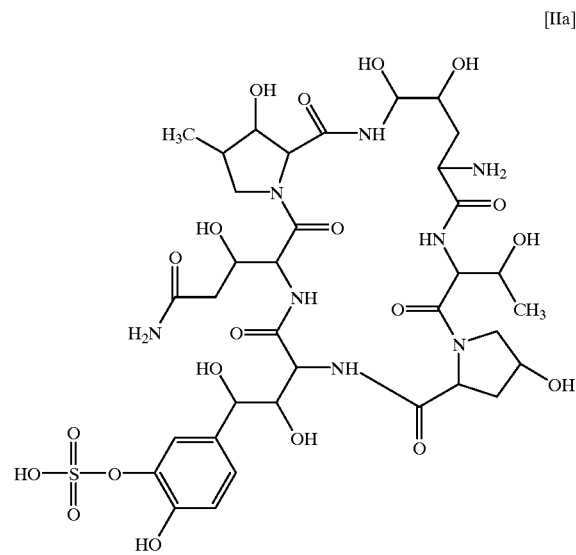

[IIa]

or a salt thereof, or an analog of FR179642 of the following general formula [II] which includes FR179642 Substance:

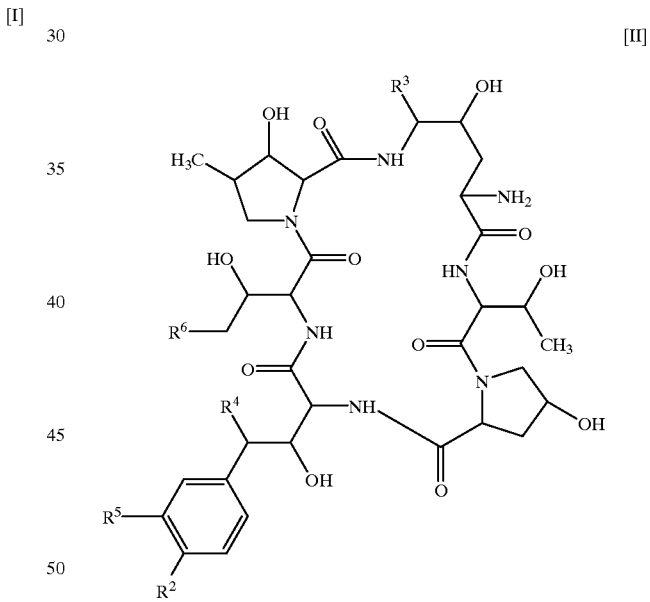

[II]

[wherein R², R³, R⁴, R⁵, and R⁶ are the same groups as respectively defined above] or a salt thereof.

The preferred species of the above-mentioned salt of compound [I] and [II] are nontoxic mono- or di-salts of the conventional types, thus including metal salts, for example alkali metal salts (e.g. sodium salt, potassium salt, etc.) and alkaline earth metal salts (e.g. calcium salt, magnesium salt, etc.), ammonium salts, salts with organic bases (e.g. trimethylamine salt, triethylamine salt, pyridine salt, picoline salt, dicyclohexylamine salt, N,N'-dibenzylethylenediamine salt, etc.), organic acid addition salts (e.g. formate, acetate, trifluoroacetate, maleate, tartarate, methanesulfonate, benzenesulfonate, toluenesulfonate, etc.), inorganic acid addition salts (e.g. hydrochloride, hydrobromide, hydroiodide, sulfate, phosphate, etc.) and salts with amino acids (e.g. arginine, aspartic acid, glutamic acid, etc.).

The preferred examples of "lower alkyl" may include straight-chain or branched-chain alkyl groups containing 1~6 carbon atom(s), such as methyl, ethyl, propyl, isopropyl, butyl, isobutyl, tert-butyl, pentyl, isopentyl and hexyl. The more preferred one may be $C_{1-4}$ alkyl, and the still more preferred one may be methyl.

The preferred example of "higher alkyl" may include straight-chain or branched-chain alkyl groups containing 7~20 carbon atom(s), such as heptyl, octyl, 3,5-dimethyloctyl, 3,7-dimethyloctyl, nonyl, decyl, undecyl, dodecyl, tridecyl, tetradecyl, pentadecyl, hexadecyl, heptadecyl, octadecyl, nonadecyl and eicosyl.

The preferred example of "lower alkoxy" may include straight-chain or branched-chain alkoxy groups such as methoxy, ethoxy, propoxy, isopropoxy, butoxy, isobutoxy, tert-butoxy, pentyloxy, tert-pentyloxy, neopentyloxy, hexyloxy and isohexyloxy.

The preferred example of "higher alkoxy" may include straight-chain or branched-chain groups such as heptyloxy, octyloxy, 3,5-dimethyloctyloxy, 3,7-dimethyloctyloxy, nonyloxy, decyloxy, undecyloxy, dodecyloxy, tridecyloxy, tetradecyloxy, hexadecyloxy, heptadecyloxy, octadecyloxy, nonadecyloxy and eicosyloxy.

The preferred examples of "aryl" may include phenyl optionally having lower alkyl (e.g. phenyl, mesityl, tolyl, etc.), naphthyl and anthryl, among others.

The "acyl" moiety of the preferred species of "acylamino" or "acyl" may include aliphatic acyl groups derived from carboxylic acids, carbonic acids, carbamic acids, sulfonic acids, etc., aromatic acyl, heterocyclic-acyl, aryl-substituted aliphatic acyl, and heterocyclic-substituted aliphatic acyl.

The preferred examples of said "acyl" moiety may include aryl (e.g. phenyl, napthyl, anthryl, etc.) which may have one or more (preferably 1~3) suitable substituent(s) such as halogen (e.g. fluoro, chloro, bromo, iodo), hydroxy, said higher alkoxy and said aryl; said lower alkoxy; amino; protected amino [preferably acylamino, such as lower alkoxycarbonylamino (e.g. methoxycarbonylamino, ethoxycarbonylamino, propoxycarbonylamino, butoxycarbonylamino, t-butoxycarbonylamino, pentyloxycarbonylamino, hexyloxycarbonylamino, etc.) etc.]; di(lower)alkylamino (e.g. dimethylamino, N-methylethylamino, diethylamino, N-propylbutylamino, dipentylamino, dihexylamino, etc.); lower alkoxyimino (e.g. methoxyimino, ethoxyimino, propoxyimino butoxyimino, t-butoxyimino, pentyloxyimino, hexyloxyimino, etc.); ar(lower)alkoxyimino such as phenyl(lower)alkoxyimino which may have one or more (preferably 1~3) suitable substituent(s) such as said higher alkoxy (e.g. benzyloxyimino, phenethyloxyimino, benzhydryloxyimino, etc.); heterocyclicthio (preferably pyridylthio) which may have one or more (preferably 1~3) suitable substituent(s) such as higher alkyl (e.g. heptyl, octyl, 2-ethylhexyl, nonyl, decyl, 3,7-dimethtyloctyl, undecyl, dodecyl, tridecyl, tetradecyl, pentadecyl, 3-methyl-10-ethyldodecyl, hexadecyl, heptadecyl, octadecyl, nonadecyl, eicosyl, etc.); lower alkanoyl (e.g. formyl, acetyl, propionyl, butyryl, isobutyryl, valeryl, hexanoyl, pivaloyl, etc.) which may have one or more (preferably 1~3) suitable substituent(s) such as heterocyclic group (e.g. thienyl, imidazolyl, pyrazolyl, furyl, tetrazolyl, thiazolyl, thiadiazolyl, etc.) which, in turn, may have one or more (preferably 1~3) suitable substituent(s) such as amino, said protected amino, said higher alkyl, etc.;

higher alkanoyl (e.g. heptanoyl, octanoyl, nonanoyl, decanoyl, undecanoyl, lauroyl, tridecanoyl, myristoyl, pentadecanoyl, palmitoyl, 10,12-dimethyltetradecanoyl, heptadecanoyl, stearoyl, nonadecanoyl, eicosanoyl, etc.); lower alkenoyl (e.g. acryloyl, methacryloyl, crotonoyl, 3-pentenoyl, 6-hexenoyl, etc.) which may have one or more (preferably 1~3) suitable substituent(s) such as said aryl which, in turn, may have one or more (preferably 1~3) suitable substituent(s) such as said higher alkoxy;

higher alkenoyl (e.g. 4-heptenoyl, 3-octenoyl, 3,6-decadienoyl, 3,7,11-trimethyl-2,6,10-dodecatrienoyl, 4,10-heptadecadienoyl, etc.);

lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc.);

higher alkoxycarbonyl (e.g. heptyloxycarbonyl, octyloxycarbonyl, 2-ethylhexyloxycarbonyl, nonyloxycarbonyl, decyloxycarbonyl, 3,7-dimethylocytyloxycarbonyl, undecyloxycarbonyl, dodecyloxycarbonyl, tridecyloxycarbonyl, tetradecyloxycarbonyl, pentadecyloxycarbonyl, 3-methyl-10-ethyldodecyloxycarbonyl, hexadecyloxycarbonyl, heptadecyloxycarbonyl, octadecyloxycarbonyl, nonadecyloxycarbonyl, eicosyloxycarbonyl, etc.);

aryloxycarbonyl (e.g. phenoxycarbonyl, naphthyloxycarbonyl, etc.);

arylglyoxyloyl (e.g. phenylglyoxyloyl, naphthylglyoxyloyl, etc.);

ar(lower)alkoxycarbonyl which may have one or more suitable substituent(s), for example phenyl(lower)alkoxycarbonyl which may have nitro or lower alkoxy (e.g. benzyloxycarbonyl, phenethyloxycarbonyl, p-nitrobenzyloxycarbonyl, p-methoxybenzyloxycarbonyl, etc.);

lower alkylsulfonyl (e.g. methylsulfonyl, ethylsulfonyl, propylsulfonyl, isopropylsulfonyl, pentylsulfonyl, butylsulfonyl, etc.);

arylsulfonyl (e.g. phenylsulfonyl, naphthylsulfonyl, etc.) which may have one or more (preferably 1~3) suitable substituent(s) such as said lower alkyl, said higher alkoxy, etc.;

ar(lower)alkylsulfonyl such as phenyl(lower)alkylsulfonyl (e.g. benzylsulfonyl, phenethylsulfonyl, benzhydrylsulfonyl, etc.;

said halogen; lower alkyl (e.g. methyl, ethyl, propyl, butyl, t-butyl, pentyl, hexyl, etc.); said higher alkyl; lower alkoxy (e.g. methoxy, ethoxy, propoxy, butoxy, t-butoxy, pentyloxy, hexyloxy, etc.) which may have one or more (preferably 1~10) suitable substituent(s) such as said lower alkoxy, said halogen, said aryl, etc.; higher alkoxy (e.g. heptyloxy, octyloxy, 2-ethylhexyloxy, nonyloxy, decyloxy, 3,7-dimethyloctyloxy, undecyloxy, dodecyloxy, tridecyloxy, tetradecyloxy, pentadecyloxy, 3-methyl-10-ethyldodecyloxy, hexadecyloxy, heptadecyloxy, octadecyloxy, nonadecyloxy, eicosyloxy, etc.) which may have one or more (preferably 1~17) suitable substituent(s) such as said halogen; higher alkenyloxy (e.g. 3-heptenyloxy, 7-octenyloxy, 3,6-octadienyloxy, 5-nonenyloxy, 1-decenyloxy, 3,7-dimethyl-6-octenyloxy, 3,7-dimethyl-2, 6-octadienyloxy, 8-undecenyloxy, 3,6,8-dodecatrienyloxy, 5-tridecenyloxy, 7-tetradecenyloxy, 1,8-pentadecadienyloxy, 15-hexadecenyloxy, 11-heptadecenyloxy, 7-octadecenyloxy, 10-nonadecenyloxy, 18-eicosenyloxy, etc.); carboxy; said aryl which may have one or more (preferably 1~3) suitable substituent(s) such as said higher alkoxy; aroyl (e.g. benzoyl, naphthoyl, anthrylcarbonyl, etc.) which may have one or more (preferably 1~5) suitable substituent(s) such as aryloxy (e.g. phenoxy, naphthyloxy, anthryloxy, etc.) which, in turn, may have one or more (preferably 1~3) suitable substituent(s) such as, for example, said lower alkoxy or said higher alkoxy; and so on.

Among the above-mentioned species of "acyl", the preferred one may be higher alkanoyl, and the particularly preferred one may be palmitoyl.

The "acyl" moiety in the term of "acyloxy" can be referred to aforementioned "acyl".

The preferred example of "acyloxy" may include lower alkanoyloxy (e.g. formyloxy, acetyloxy, propionyloxy, butyryloxy, isobutyryloxy, valeryloxy, hexanoyloxy, pivaloyloxy, etc.) and phosphonoxy.

The acylase of this invention is one of the so-called inducible enzymes, and it is an essential requisite for the production of the enzyme that a cyclic lipopeptide compound of formula [I], for example FR901379 Substance, is present in the medium in the process of growth of the fungal producer of this acylase. Therefore, this acylase can be produced by culturing a fungal strain capable of producing this particular acylase, for example any of Oidiodendron sp. No. 30084, *Oidiodendron echinulatum* IFO 31963, *Oidiodendron tenuissimum* IFO 6798, *Oidiodendron truncatum* IFO 9951 and *Oidiodendron truncatum* IFO 31812, all of which belong to the genus Oidiodendron, or Verticillium sp. No. 30085 which belongs to the genus Verticillium, in the presence of said cyclic lipopeptide compound in a culture medium.

More particularly, the acylase can be produced by culturing said acylase-producing fungal strain in a nutrient medium containing one or more assimilable carbon sources and digestible nitrogen sources in the presence of said cyclic lipopeptide compound of formula [I], for example FR901379 Substance, preferably aerobically by, for example, shake culture or submerged culture.

Generally speaking, this novel acylase can be produced by culturing said novel acylase-producing fungus in an aqueous medium containing assimilable carbon and digestable nitrogen sources preferably aerobically by shake culture or submerged culture.

The preferred source of carbon to be present in the culture medium may include carbohydrates such as glucose, xylose, galactose, glycerol, starch and dextrin. As other sources of carbon, there may be mentioned maltose, rhamnose, raffinose, arabinose, mannose, salicin, sodium succinate, etc.

The preferred source of nitrogen may include yeast extract, peptone, gluten meal, cottonseed flour, soybean flour, corn steep liquor, dried yeast, wheat germ, feather powder, peanut flour, etc. and inorganic or organic nitrogen compounds such as ammonium salts, (e.g. ammonium nitrate, ammonium sulfate, ammonium phosphate, etc.) urea, amino acids, etc.

While those sources of carbon and nitrogen are preferably used in suitable combinations, it is not necessary to use pure sources, for even materials of low purity can be used only provided that they contain suitable amounts of growth factors and reasonable amounts of inorganic nutrients. This is because impure materials sometimes contain such growth factors and trace elements and, therefore, can be used with advantage. Optionally, the medium may be supplemented with sodium carbonate or calcium carbonate, sodium phosphate or potassium phosphate, sodium chloride or potassium chloride, sodium iodide or potassium iodide, magnesium salts, copper salts, cobalt salts and other inorganic salts. Particularly, when the culture medium produces a copious foam, an antifoam such as liquid paraffin, a fatty oil, vegetable oil, mineral oil or silicone oil may be added as necessary.

For the high production of this novel acylase, submerged aerobic culture is the preferred methods. For small-scale production, shake culture or surface culture in a flask or bottle is carried out. For culturing the fungus in a large tank, it is preferable to carry out a preculture and inoculate the production tank with the resulting seed culture in order that growth retardation of the fungus may be avoided. Thus, preferably a relatively small quantity of medium is inoculated with spores or hyphae of the microorganism, and the inoculated medium is incubated to prepare a seed culture in the first place, and the resulting seed culture is aseptically transferred to the large tank. The medium for use in this preparation of a seed culture may be substantially identical to or different from the medium for use in the production of the novel acylase.

The agitation and aeration of the fermentation broth can be achieved in various ways. The agitation can be achieved by using a propeller mixer or the like stirring device, rotating or reciprocating a fermentation jar, using a pump of optional construction or plowing sterile air through the medium. The aeration can be achieved by passing sterile air through the fermentation system.

The fermentation is carried out at a temperature of generally about 15~32° C. preferably 20~30° C. and a pH level of 6~8 for about 50~150 hours, although those conditions may be varied according to other conditions and scale of fermentation.

The novel acylase thuse produced can be recovered from the fermentation broth by the conventional procedures which are usually employed in the recovery of other known bioactive substances. The novel acylase thus produces occurs in both the cultured mycelium and the supernatant of the broth. Therefore, the novel acylase can be separated from the mycelium and the supernatant or filtrate available on filtration or centrifugation of the fermentation broth and purified by the conventional procedures such as concentration under reduced pressure, freeze-drying, extraction with the common solvent, pH adjustment, treatment with a conventional resin such as an anion exchange resin, a cation exchange resin, a nonionic adsorbent resin, or the like, treatment with a conventional adsorbent such as active charcoal, silicic acid, silica gel, cellulose, alumina, or the like, crystallization, and recrystallization.

Referring to the level of addition of the cyclic lipopeptide compound of the formula [I], e.g. FR9601379 Substance, which is necessary for inducing production of the enzyme, the cyclic lipopeptide compound need be available only in a minimal amount in the medium during the growth of the acylase- producing fungus and usually the objective effect can be well obtained by adding about 0.01 to 1% of the substance to the culture medium. It is not essential to add the cyclic lipopeptide to the preculture medium.

In the fermentative production of FR901379 Substance, it is possible to inoculate the FR901379 production medium with an FR901379-producing strain and said acylase-producing strain concurrently or at staggered times so as to let FR179642 Substance be directly produced in the broth.

The following examples are intended to illustrate but by no means delimit the deacylation technology of the invention which comprises the use of the acylases produced by the fungi Oidiodendron sp. No. 30084, *Oidiodendron echinulatum* IFO 31963, *Oidiodendron tenuissimum* IFO 6798, *Oidiodendron truncatum* IFO 9951, *Oidiodendron truncatum* IFO 31812 and Verticillium sp. No. 30085.

Process for production of the acylase

EXAMPLE 1-1

Production of the acylase elaborated by Oidiodendron sp. No. 30084

As the preculture medium, a medium comprising glucose 1%, soluble starch 2%, cottonseed flour 3%, soybean flour 1.5%, potassium dihydrogenphosphate 1% and calcium carbonate 0.2% was used. As the production medium, a medium comprising glucose 6%, yeast extract 1% and potassium dihydrogenphosphate 0.1% (adjusted to pH 6.0 before sterilization) was used.

A 100-ml conical flask containing 30 ml of said preculture medium was sterilized by autoclaving at 120° C., for 20 minutes. After cooling to room temperature, the flask was inoculated with 1~2 loopfuls of a slant agar culture of Oidiodendron sp. No. 30084. After cooling to room temperature, shake culture was carried out at 25° C., for 7 days to prepare a seed culture. Then, a 500-ml conical flask containing 100 ml of said production medium was sterilized at 120° C., for 20 minutes and cooled to room temperature, and FR901379 Substance was aseptically added at a final concentration of 0.1%. The flask was then inoculated with 2 ml of said seed culture and incubated with shaking at 30° C. for 3 days to provide an anzyme broth.

EXAMPLE 1-2

Production of the acylase elaborated by Verticillium sp. No. 50085

As the preculture medium, a medium comprising glucose 1%, soluble starch 2%, cottonseed flour 3%, soybean flour 1.5%, potassium dihydrogen phosphate 1% and calcium carbonate 0.2% was used. As the production medium, a medium comprising glucose 6%, yeast extract 1% and potassium dihydrogenphosphate 0.1% (adjusted to pH 6.0 before sterilization) was used.

A 100-ml conical flask containing 30 ml of said preculture medium was sterilized by autoclaving at 120° C. for 20 minutes. After cooling to room temperature, the flask was inoculated with 1~2 loopfuls of a slant agar culture of Verticillium sp. No. 30085. After cooling to room temperature, shake culture was carried out at 25° C., for 7 days to prepare a seed culture. Then, a 500-ml conical flask containing 100 ml of said production medium was sterilized at 120° C. for 20 minutes and cooled to room temperature, and FR901379 substance was aseptically added at a final concentration of 0.1%. The flask was then inoculated with 2 ml of said seed culture and incubated with shaking at 30° C., for 4 days to provide an enzyme broth.

EXAMPLE 1-3

Production of the acylase elaborated by *Oidiodendron tenuissimum* IFO 6798 allotted from Institute for Fermentation, Osaka (2-17-85, Juso-Hommachi, Yodogawa-ku, Osaka).

As the preculture medium, a medium comprising glucose 1%, soluble starch 2%, cottonseed fluor 3%, soybean flour 1.5%, potassium dihydrogenphosphate 1% and calcium carbonate 0.2% was used. As the production medium, a medium comprising modified starch 6%, corn steep liquid 6% and potassium dihydrogenphosphate 0.1% was used.

A 500-ml conical flask containing 100 ml of said preculture medium was sterilized by autoclaving at 120° C. for 20 minutes. After cooling to room temperature, the flask was inoculated with 1~2 loopfuls of an agar plate culture of *Oidiodendron tenuissimum* IFO 6798 and incubated at 25° C. for 4 days to prepare a seed culture. Then, a 500 ml conical flask containing 100 ml of said production medium was sterilized by autoclaving at 120° C. for 20 minutes and cooled to room temperature, and FR901379 Substance was aseptically added at a final concentration of 0.1%. The flask was then inoculated with 5 ml of said seed culture, and shake culture was carried out at 25° C., for 4 days to provide an enzyme broth.

EXAMPLE 1-4

Production of the acylases elaborated by subcultured strains belonging to the genus Oidiodendron Using the following subcultured strains belonging to the genus Oidiodendron as allotted from Institute for Fermentation, Osaka (2-17-85, Juso-Hommachi, Yodogawa-ku, Osaka), enzyme broths could be obtained according to a similar manner to that of Example 1-1 just as in the case of Oidiodendron sp. No. 30084.

*Oidiodendron echinulatum* IFO 31963
*Oidiodendron truncatum* IFO 9951
*Oidiodendron truncatum* IFO 31812

EXAMPLE 2

Purification of the acylase elaborated by *Oidiodendron tenuissimum* IFO 6798

The enzyme fermentation broth obtained in Example 1-3 was adjusted to pH 3 and centrifuged at low temperature. The resulting supernatant was passed through an SP207 column. The effluent was filtered through a UF membrane (Asahi Chemical Industry, AIP-1010) into 20 mM Tris-HCl buffer (pH 7). This solution was applied onto a DEAE-Toyopearl column (Tosoh, Cl⁻ form), and elution was carried out with 20 mM citrate buffer (pH 5). After the active fraction was adjusted to pH 4, 0.6 M equivalent of $(NH_4)_4SO_4$ was added and dissolved, and the solution was further applied onto a Phenyl-Toyopearl column (Tosoh) eluting with 0.2 M $(NH_4)_2SO_4$-containing 20 mM citrate buffer (pH 4). The active fraction was desalted and concentrated using a DF membrane (Asahi Chemical Industry, SIP-0013). The desalted concentrate was subjected to gel permeation chromatography of a YMC-Diol column (YMC) (mobile phase; 0.1 M NaCl-50 mM acetate buffer, pH 5). The purified acylase was subjected to SDS-PAGE. As a result, the enzyme converged into a band corresponding to about 40 kD. The molecular weight of the acylase as determined by gel filtration-HPLC with TSKgel G3000PWXL (Tosoh) was about 150 kD. Those results suggested that the acylase is an enzyme protein of about 150 kD having identical or different subunits of about 40 kD.

The HPLC comprising a variable wavelength UV detector, a pump, and an integrator was used. As the column, a TSK gel G3000 PWXL column (7.8 mm I.D.×30 cm) was used. Using a mobile phase consisting in 0.1 M phosphate buffer (pH 6)+0.3 M NaCl, the enzyme protein was eluted at a flow rate of 0.5 mL/min. The molecular weight markers were chymotrypsinogen A (25 kD), ovalbumin (43 kD), albumin (67 kD) and aldolase (158 kd). The retention time under the above conditions was about 17.9 minutes and by reference to a calibration curve constructed with the markers, its molecular weight was estimated to be about 150 kD.

The process for deacylating the acyl side chain of the antifungal cyclic lipopeptide compound (e.g. FR901379 Substance) which comprises the use of the acylase according to the invention is now described in detail.

This acyl side chain deacylation process was carried out by adding the fermentation broth obtained as above to the cyclic lipopeptide compound (e.g. FR901379 Substance) and incubating the mixture at a reaction temperature of 10° C. to 50° C. and a pH level of about 2 to 6, and detecting and separating the resulting cyclic peptide (e.g., FR179642 Substance) by high performance liquid chromatography (HPLC).

The following examples are intended to specifically illustrate but by no means delimit the deacylation technology of this invention.

EXAMPLE 3-1

To 7 ml of the fermentation broth of Oidiodendron sp. No. 30084 obtained in Example 1-1 was added 1 ml of an aqueous solution (20 ml/ml) of FR901379 Substance (20 mg as FR901379 Substance; 16.7 µmol) as well as 2 ml of a buffer (0.2 M sodium citrate buffer, pH 4.0), and the reaction was carried out at 30° C. for 3 hours. The reaction was then stopped by adding 0.4 M trichloroacetic acid and centrifuged at low speed to remove precipitated high molecular weight protein and other impurities. The FR179642 Substance produced was subjected to HPLC and monitored at 210 nm to determine the acylase activity.

The HPLC comprised of a variable wavelength UV retector (Hitachi L-4000), a pump (Hitachi L-6000) and an integrator (Hitachi D-2500) was used. As the stationary phase, LiChrospher 100RP-18 (250 mm×4 mm i.d., particle dia. 5 mm) was used. Using a mobile phase consisting in 5% acetonitrile/0.5% ammonium dihydrogenphosphate, FR179642 Substance was eluted at a flow rate of 1 ml/min. The retention time of FR179642 Substance was about 6.3 minutes. The yield of FR179642 Substance as calculated from the data was 4.5 mg (4.8 $\mu$mol).

EXAMPLE 3-2

To 7 ml of the fermentation broth of Verticillium sp. No. 30085 obtained in Example 1-2 was added 1 ml of an aqueous solution (20 mg/ml) of FR901379 Substance (20 mg as FR901379 Substance/ml; 16.7 $\mu$mol) as well as 2 ml of a buffer (0.2 M sodium citrate buffer, pH 4.0), and the reaction was carried out at 30° C. for 1 hour. The reaction was then stopped with 0.4 M trichloroacetic acid, and the mixture was centrifuged at low speed to remove high molecular weight protein and other impurities as a precipitate. The supernatant was subjected to HPLC and the product FR179642 Substance being monitored, at 210 nm to determine the acylase activity.

The HPLC comprised of a variable wavelength UV detector (Hitachi L-4000), a pump (Hitachi L-6000) and an integrator (Hitachi D-2500) was used. As the stationary phase, LiChrospher 100RP-18 (250 mm×4 mm i.e., particle dia. 5 mm) was used. Using a mobile phase consisting in 5% acetonitrile/0.5% ammonium dihydrogenphosphate, FR179642 Substance was eluted at a flow rate of 1 ml/min. The retention time of FR179642 Substance was about 6.3 minutes. The yield of FR179642 Substance as calculated from the data was 7 mg (7.5 $\mu$mol).

EXAMPLE 3-3

To 50 $\mu$l of the enzyme broth prepared by the procedure described in Example 2 was added 100 $\mu$l of an aqueous solution (100 mg/ml) of FR901379 Substance (10 mg as FR901379 Substance/ml; 8.35 $\mu$mol) as well as 100 $\mu$l of methanol, 100 $\mu$l of a buffer (0.5 M citrate buffer, pH 4) and 650 $\mu$l of water, and the reaction was carried out at 30° C. for 30 minutes. The reaction was stopped by adding 1 ml of 4% acetic acid and 2 ml of methanol, and the reaction mixture was subjected to HPLC. The product FR179642 Substance was monitored at 215 nm, and the acylase activity was determined. The HPLC was comprised of a variable wavelength UV detector (Shimadzu SPD-10A), a pump (Shimadzu LC-10AD) and an integrator (Shimadzu C-R6A), and as the stationary phase, Haseisorb lCPO Super (200 mm×4.6 mm i.d., Tokyo Kasei) was used. Using 4% methanol/0.1% phosphoric acid at 40° C. as the mobile phase, FR179642 Substance was eluted at a flow rate of 1.2 ml/min. The retention time of FR179642 Substance was about 6 minutes. The yield of FR179642 Substance as calculated from the data was 400 $\mu$g, (0.43 $\mu$mol).

EXAMPLE 3-4

To 50 $\mu$l of the enzyme solution as purified by the procedure described in Example 1 was added 100 $\mu$l of a solution of Echinocandin B substance (in dimethyl sulfoxide, 100 mg/ml) (10 mg as Echinocandin B substance/ml) as well as 100 $\mu$l of a buffer (0.5 M citrate buffer, pH 4) and 750 $\mu$l of water, and the reaction was carried out at 30° C. for 30 minutes. The reaction was stopped by adding 1 ml of 4% acetic acid and 2 ml of methanol, and the product Echinocandin B nuclear substance was assayed by HPLC. The HPLC used was comprised of a variable wavelength UV detector (Shimadzu SPD-10A), a pump (Shimadzu LC-10AD) and an integrator (Shimadzu C-R6A), and using LiChrosphr 100RP-18(e) (250 mm×4 mm i.d., particle dia. 5 $\mu$m, E.Merck) as the stationary phase and 5% acetonitrile/ 0.5% ammonium phosphate at 40° C., as the mobile phase, Schinocandin B nuclear substance was eluted at a flow rate of 1.0 ml/min. The retention time of Echinocandin B nuclear substance was about 6 minutes. The yield of Echinocandin B nuclear substance as calculated from the data was 3.1 $\mu$g (0.004 $\mu$mol).

EXAMPLE 3-5

To 50 $\mu$l of the enzyme solution as purified in Example 2 was added 100 $\mu$l of a solution of Aculeacin A (in dimethyl sulfoxide, 100 mg/ml) (10 mg as Aculeacin A substance/ml) as well as 100 $\mu$l of a buffer (0.5 M citrate buffer, pH 4) and 750 $\mu$l of water, and the reaction was carried out at 30° C., for 30 minutes. The reaction was stopped by adding 1 ml of 4% acetic acid and 2 ml of methanol, and the production Aculeacin A nuclear substance (=Echinocandin B nuclear substance) was assayed by HPLC. The HPLC was comprised of a variable wavelength UV detector (Shimadzu SPD-10A), a pump (Shimadzu LC-10AC) and an integrator (Shimadzu C-R6A), and using LiChrospher 100RP-18(e) (250 mm×4 mm i.d., particle dia. 5 $\mu$m, E.Merck) as the stationary phase and 5% acetonitrile/0.5% ammonium phosphate at 40° C. as the mobile phase, Aculeacin A nuclear substance was eluted at a flow rate of 1.0 ml/min. The retention time of Aculeacin A nuclear substance was about 6 minutes. The yield of Aculeacin A nuclear substance as calculated from the data was 17.7 $\mu$g (0.022 $\mu$mol).

EXAMPLE 3-8

To 700 $\mu$l of the fermentation broth obtained by using *Oidiogandron trundatum* IFO 9951 in Example 3-4 was added 100 $\mu$l of an aqueous solution (100 mg/ml) of FR901379 Substance (10 mg as FR901379 Substance/ml; 8.35 $\mu$mol) as well as 200 $\mu$l of a buffer (0.2 M citrate buffer, pH 4), and the reaction was carried out at 30° C. for 60 minutes. The reaction was stopped by adding 1 ml of 4% acetic acid and 2 ml of methanol, and the mixture was filtered through a membrane filter (0.45 $\mu$m) to remove high molecular weight protein and other impurities. The filtrate was subjected to HPLC and the product FR179642 Substance was monitored at 215 nm to determine the acylase activity.

The HPLC was comprised of a variable wavelength UV detector (Shimadzu SPD-10A), a pump (Shimadzu LC-10AD) and an integrator (Shimadzu C-R6A), and using Kaseisorb LC PO Super (200 mm×4.6 mm i.d., Tokyo Kasei) as the stationary phase and 4% methanol/0.1% phosphoric acid at 40° C. as the mobile phase, the product FR1798642 Substance was eluted at a flow rate of 1.2 ml/min. The retention time of FR179642 Substance was about 6 minutes. The yield of FR179642 Substance as calculated from the data was 232 $\mu$g/ml (0.25 $\mu$mol/ml).

EXAMPLE 3-7

Using the procedure described in Example 3-6, FR179642 Substance could be obtained from the culture of

*Oidiodendron truncatum* IFO 31812 as obtained in Example 1–4 as well. The calculated yield of FR179642 Substance was 266 μg (0.28 μmol).

EXAMPLE 3-8

Using the procedure described in Example 3-6, FR179642 Substance could be obtained from the culture of *Oidiodendron echinulatum* IFO 31963 as obtained in Example 1–4 as well. The calculated yield of FR179642 Substance was 136 μg (0.15 μmol).

The characteristics of the process of deacylation of the acyl side chain of an antifungal cyclic lipopeptide compound (e.g. FR901379 Substance) by the fungal acylase are now described.

The data presented were generated by the experimental procedures described in Example 3-1 through Example 3-5 with modification of conditions such as the buffer (0.2 M~0.5 M sodium citrate buffer, potassium phosphate buffer, and Tris-HCl buffer in suitable combinations), the reaction temperature, and the concentration of potassium chloride added. The acylase activity was expressed in the concentration (determined by HPLC) of FR179642 Substance or Echinocandin B nuclear substance at completion of the reaction.

Optimum reaction pH

TEST EXAMPLE 1-1

The optimum pH for the acylase elaborated by Oidiodendron sp. No. 30084

The influence of reaction pH on the concentration of FR179642 Substance at completion of the reaction was studied using the same procedure as Example 3-1. The results are shown in Table 3.

TABLE 3

| pH | Concentration of FR179642 Substance at completion of reaction (μg/ml) |
| --- | --- |
| 3 | 590 |
| 4 | 450 |
| 5 | 210 |
| 6 | 70 |
| 7 | −5* |
| 8 | −2* |
| 9 | 0 |

*: caused by measurement error

TEST EXAMPLE 1-2

The optimum pH for the acylase elaborated by Verticillium sp. No. 30085

The influence of reaction pH on the concentration of FR179642 Substance at completion of the reaction was studied using the same procedure as Example 3-2. The results are shown in Table 4.

TABLE 4

| pH | Concentration of FR179642 Substance at completion of reaction (μg/ml) |
| --- | --- |
| 3 | 480 |
| 4 | 520 |
| 5 | 410 |
| 6 | 100 |
| 7 | 10 |

TABLE 4-continued

| pH | Concentration of FR179642 Substance at completion of reaction (μg/ml) |
| --- | --- |
| 8 | −10* |
| 9 | −20* |

*: caused by measurement error

The above results indicate that, in the working of the invention, the optimum reaction pH is 2 to 6, preferably 3 to 5, for both acylases.

TEST EXAMPLE 1-3

The optimum pH for the acylase elaborated by *Oidiodendron tenuissimum* IFO 6798

The influence of reaction pH on the concentration of FR179642 Substance at completion of the reaction was studied using the same procedure as Example 3-3. The results are shown in Table 5.

TABLE 5

| pH | Concentration of FR179642 Substance at completion of reaction (μg/ml) |
| --- | --- |
| 2 | 434 |
| 3 | 422 |
| 4 | 366 |
| 5 | 312 |
| 6 | 65 |
| 7 | 0 |
| 8 | 0 |

TEST EXAMPLE 1-4

The optimum pH for the acylase elaborated by *Oidiodendron tenuissimum* IFO 6798

The influence of reaction pH on the concentration of Echinocandin B nuclear substance at completion of the reaction was studied using the same procedure as Example 3-4. The results are shown in Table 6.

TABLE 6

| pH | Concentration of Echinocandin B nuclear substance at completion of reaction (μg/ml) |
| --- | --- |
| 2 | 2.5 |
| 3 | 2.8 |
| 4 | 2.6 |
| 5 | 1.4 |
| 6 | 0.16 |
| 7 | 0.17 |
| 8 | 0.14 |

Regardless of substrates, the reaction was considerably retarded in the neutral and higher pH range. When FR901379 was used as the substrate, the reaction rate increased with declining pH. When Echinocandin B was used as the substrate, high reaction rates were obtained within the pH range of 2~4.

The above results (Test Examples 1-3 and 1-4) indicate that with whichever of the substrates, the optimum reaction pH is 2~6, most preferably 2~4. It is also clear that the reaction does not substantially proceed in the neutral and higher pH region.

Optimum reaction temperature

TEST EXAMPLE 2-1

The optimum temperature for the acylase elaborated by Oidiodendron sp. No. 30084

The influence of reaction temperature on the concentration of FR179642 Substance at completion of the reaction was studied using the procedure of Example 3-1. The results are shown in Table 7.

TABLE 7

| Temperature | Concentration of FR179642 Substance at completion of reaction (µg/ml) |
|---|---|
| 20 | 190 |
| 25 | 280 |
| 30 | 460 |
| 35 | 550 |
| 40 | 600 |
| 45 | — |
| 50 | 280 |

TEST EXAMPLE 2-2

The optimum temperature for the acylase elaborated by Verticillium sp. No. 30085

The influence of reaction temperature on the concentration of FR179642 Substance at completion of the reaction was studied using the procedure of Example 3-2. The results are shown in Table 8.

TABLE 8

| Temperature | Concentration of FR179642 Substance at completion of reaction (µg/ml) |
|---|---|
| 20 | 250 |
| 25 | 470 |
| 30 | 700 |
| 35 | — |
| 40 | 780 |
| 45 | — |
| 50 | 440 |

The above results indicate that for both acylases the optimum reaction temperature is 20~50° C., preferably 30~40° C.

TEST EXAMPLE 2-3

The optimum temperature for the acylase elaborated by *Oidiodendron tenuissimum* IFO 6798

The influence of reaction temperature on the concentration of FR179642 Substance at completion of the reaction was studied using the procedure of Example 3-3. The results are shown in Table 9.

TABLE 9

| Temperature | Concentration of FR179642 Substance at completion of reaction (µg/ml) |
|---|---|
| 25 | 243 |
| 30 | 383 |
| 35 | 606 |
| 40 | 828 |
| 45 | 379 |
| 50 | 80 |
| 55 | 30 |
| 60 | 22 |

TEST EXAMPLE 2-4

The optimum temperature for the acylase elaborated by *Oidiodendron tenuissimum* IFO 6798

The influence of reaction temperature on the concentration of Echinocandin B nuclear substance at completion of the reaction was studied using the same procedure as Example 3-4. The results are shown in Table 10.

TABLE 10

| Temperature | Concentration of Echinocandin B nuclear substance at completion of reaction (µg/ml) |
|---|---|
| 25 | 1.8 |
| 30 | 2.7 |
| 35 | 4.2 |
| 40 | 4.8 |
| 45 | 3.2 |
| 50 | 0.5 |
| 55 | 0.3 |
| 60 | 0.2 |

Regardless of substrates, the reaction proceeded satisfactorily at 25~45° C. and the highest reaction rate was obtained at 40° C.

Results of addition of a solvent to the reaction system

TEST EXAMPLE 3-1

The effect of addition of methanol to the reaction system involving the acylase elaborated by *Oidiodendron tenuissimum* IFO 6798

The effect of addition of methanol to the reaction system on the concentration of FR179642 Substance at completion of the reaction was studied using the procedure of Example 3-3. The results are shown in Table 11.

TABLE 11

| Concentration of methanol (%) | Concentration of FR179642 Substance at completion of reaction (µg/ml) |
|---|---|
| 0 | 273 |
| 5 | 360 |
| 10 | 400 |
| 20 | 407 |
| 30 | 332 |
| 40 | 69 |
| 50 | 0 |

TEST EXAMPLE 3-2

The effect of addition of dimethyl sulfoxide to the reaction system involving the acylase elaborated by *Oidiodendron tenuissimum* IFO 6798

The effect of addition of dimethyl sulfoxide to the reaction system on the concentration of Echinocandin B nuclear substance at completion of the reaction was studied using the procedure of Example 3-4. The results are shown in Table 12

TABLE 12

| Concentration of dimethyl sulfoxide (%) | Concentration of Echinocandin B nuclear substance at completion of reaction (µg/ml) |
|---|---|
| 0 | n.t.* |
| 5 | 2.8 |
| 10 | 3.1 |
| 20 | 3.8 |
| 30 | 3.5 |
| 40 | 1.0 |
| 50 | 0.1 |

*n.t. = not tested

When FR901379 was used as the substrate, the reaction rate was increased in the presence of 10~20% of methanol.

When Echinocandin B was used as the substrate, the reaction rate was increased on addition of 20~30% of dimethyl sulfoxide.

Influence of salt concentration

TEST EXAMPLE 4-1

The influence of salt (KCl) concentration on the reaction involving the acylase elaborated by *Oidiodendron tenuissimum* IFO 6798

The influence of salt (KCl) concentration in the reaction system on the concentration of FR179642 Substance at completion of the reaction was investigated using the procedure of Example 3-3. The results are shown in Table 13.

TABLE 13

| Concentration of KCl (M) | Concentration of FR179642 Substance at completion of reaction (µg/ml) |
|---|---|
| 0 | 369 |
| 0.3 | 352 |
| 0.6 | 336 |
| 0.9 | 343 |
| 1.2 | 317 |
| 1.5 | 326 |
| 1.8 | 315 |

TEST EXAMPLE 4-2

The influence of salt (KCl) concentration on the reaction involving the acylase elaborated by *Oidiodendron tenuissimum* IFO 6798

The influence of salt (KCl) concentration in the reaction system on the concentration of Echinocandin B nuclear substance at completion of the reaction was investigated using the procedure of Example 3-4. The results are shown in Table 14.

TABLE 14

| Concentration of KCl (M) | Concentration of Echinocandin B nuclear substance at completion of reaction (µg/ml) |
|---|---|
| 0 | 2.7 |
| 0.3 | 2.2 |
| 0.6 | 2.1 |
| 0.9 | 2.1 |
| 1.2 | 2.0 |
| 1.5 | 1.7 |
| 1.8 | 1.7 |

The addition of KCl had no effect.

It can be estimated from the above data that Km is 1590 µM and Vmax is 4.2 U/mg-protein when the reaction is carried out using FR901379 Substance as the substrate under the conditions of reaction temperature=40° C., reaction pH=3 and reaction time=15 minutes. The amount of the enzyme yielding 1 µmol of FR179642 Substance per minute was taken as 1 U.

The cyclic lipopeptide acylase obtainable by growing an acylase-producing strain belonging to the genus Oidiodendron is specifically described below.

Characteristics of the acylase derived from *Oidiodendron tenuissimum* IFO 6798

1) Activity:
The enzyme catalyzes deacylation of the fatty acyl moiety of a cyclic lipopeptide compound represented by FR901379 Substance and FR901379 analogs such as Echinocandin B, Aculeacin A, etc.

2) Optimum pH: pH 2~4
3) Optimum range of temperature for action: 25~45° C.
4) Inhibition, activity and stabilization:
Methanol: concentration-dependent activity up to 20% in the reaction mixture and inhibition at and over 40%.
5) Molecular mass:
It is considered to be an enzyme protein of about 150 kD which has identical or different subunits of about 40 kD.
6) Vmax and Km values
Km is 1590 µM and Vmax is 4.2 U/mg-protein when determined using FR901379 Substance as the substrate under the conditions of reaction temperature=40° C., reaction pH=3 and reaction time=15 minutes.
7) Substrate specificity
The deacylating activities for Echinocandin B and Aculeacin A as substrates are less potent than the activity for FR901379.

Coleophoma sp. F-11899 which elaborates FR901379 Substance and the fungal strain Oidiodendron sp. No. 30084 and fungal strain Verticillium sp. No. 30085, both of which are producers of the acylase of the invention, have been deposited with National Institute of Bioscience and Human Technology (NIBH, Higashi 1-1-3, Tsukuba-shi, Ibaraki, Japan).

| Microorganism | Accession No. |
|---|---|
| Coleophoma sp. F-11899 | FERM BP-2635 |
| Oidiodendron sp. No. 30084 | FERM BP-5943 |
| Verticillium sp. No. 30055 | FERM BP-5944 |

What is claimed is:

1. An isolated cyclic lipopeptide acylase produced by Verticillium sp. No. 30085, which catalyzes deacylation of the acyl group $R^1$ of a cyclic lipopeptide compound of the following general formula (I):

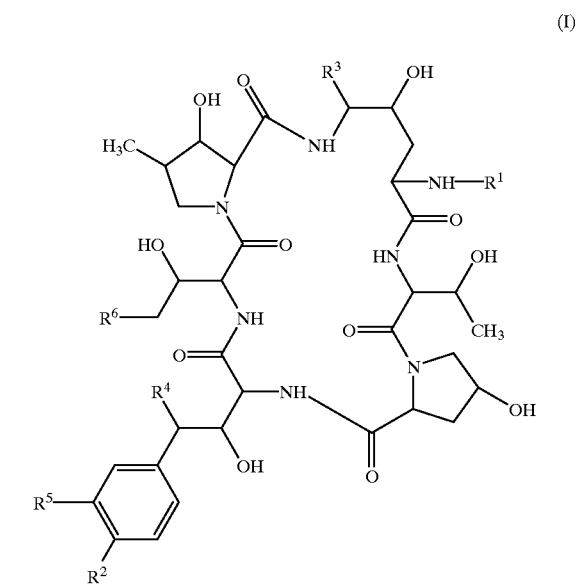

(I)

wherein
$R^1$ is acyl;
$R^2$ is hydroxy or acyloxy;

$R^3$ is hydrogen or hydroxy;
$R^4$ is hydrogen or hydroxy;
$R^5$ is hydrogen or hydroxysulfonyloxy; and
$R^6$ is hydrogen or carbamoyl or a salt thereof, to give a cyclic peptide of the following general formula (II):

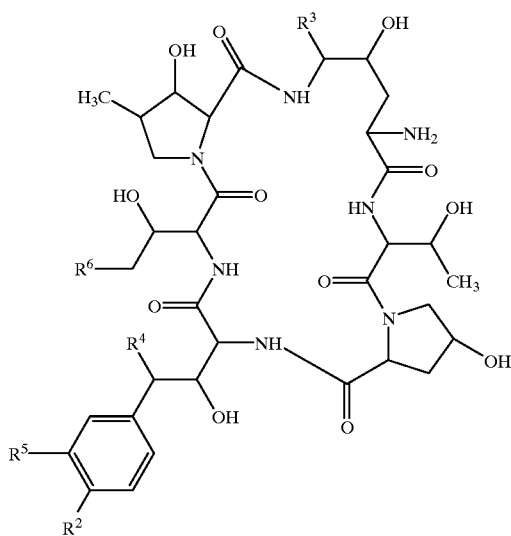

(II)

wherein $R^2$, $R^3$, $R^4$, $R^5$, and $R^6$ are the same groups as respectively defined above or a salt thereof; wherein the optimum pH for deacylation is from 3 to 5; the optimum temperature for deacylation is from 25 to 50° C.

2. The acylase according to claim 1 which catalyzes deacylation of the acyl group $R^1$ of a cyclic lipopeptide compound of the following general formula: [I]:

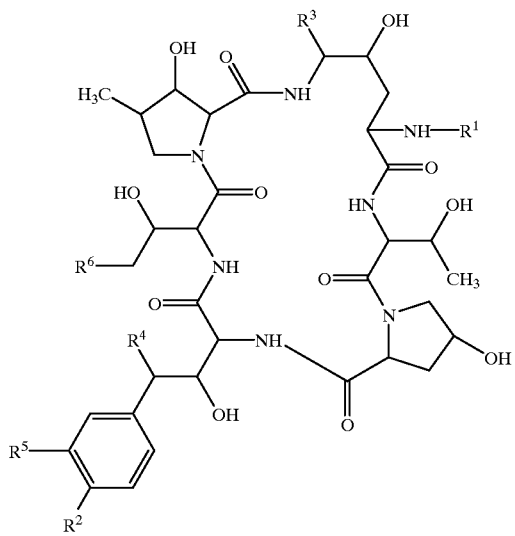

[I]

wherein
  $R^1$ is acyl;
  $R^2$ is hydrogen or acyloxy;
  $R^3$ is hydrogen or hydroxy;

or a salt thereof, to give a cyclic peptide of the following general formula:

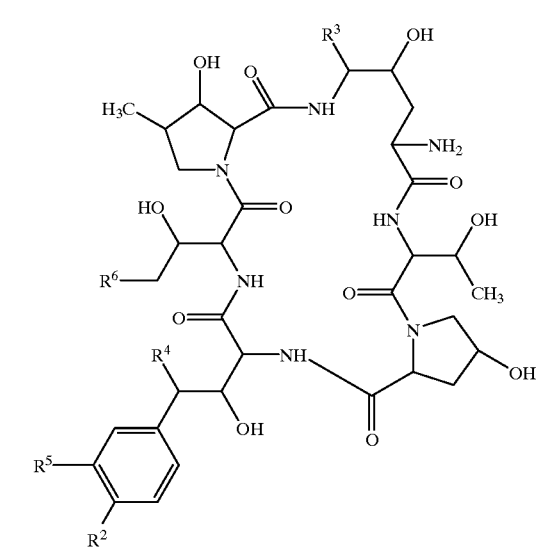

[II]

or a salt thereof.

3. The isolated acylase of claim 1, wherein
  $R^5$ is hydroxysulfonyl, and
  $R^6$ is carbamoyl.

4. A process for producing a cyclic peptide compound or a salt thereof which comprises contacting a cyclic lipopeptide compound or salt thereof with the isolated acylase of claim 1 to deacylate the fatty acyl moiety of the substrate.

5. The isolated enzyme of claim 1, wherein said cyclic lipopeptide compound is selected from the group consisting of FR901379, Echinocandin B, and Aculeacin A.

6. The process of claim 4, wherein said cyclic lipopeptide has the following formula (I):

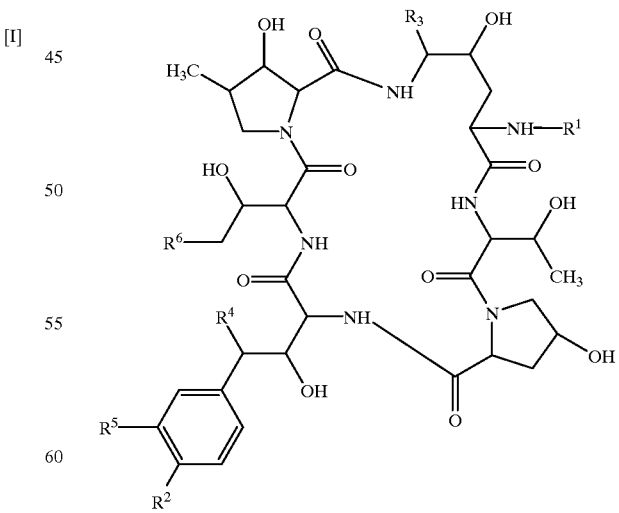

(I)

$R^4$ is hydrogen or hydroxy;

$R^5$ is hydrogen or hydroxysulfonyloxy; and $R^6$ is hydrogen or carbamoyl or a salt thereof.

7. The process of claim 4, wherein said cyclic peptide has the formula (II):

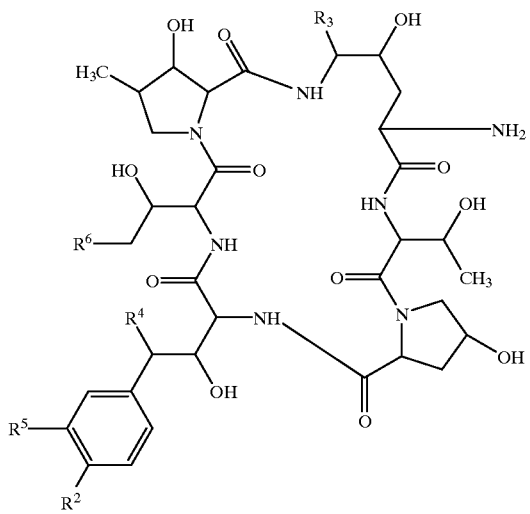

(II)

wherein $R^1$ is acyl;

$R^2$ is hydroxy or acyloxy;

$R^3$ is hydrogen or hydroxy;

$R^4$ is hydrogen or hydroxy;

$R^5$ is hydrogen or hydroxysulfonyloxy; and $R^6$ is hydrogen or carbamoyl or a salt thereof.

8. The process of claim 4, wherein said cyclic lipopeptide compound is selected from the group consisting of FR901379, Echinocandin B, and Aculeacin A.

9. A process of producing a cyclic peptide compound or a salt thereof which comprises:

culturing the strain Verticillium sp No. 30085 for a time and under conditions for the expression of an cyclic lipopeptide acylase;

isolating said cyclic lipopeptide acylase as a crude or purified enzyme solution;

contacting said cyclic lipopeptide acylase with a cyclic lipopeptide compound or salt thereof to deacylate the fatty acyl moiety of the substrate.

10. The process of claim 9, wherein said cyclic lipopeptide has the following formula (I):

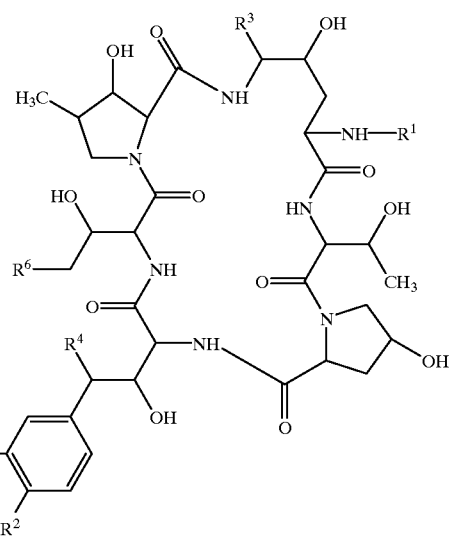

(I)

wherein $R^1$ is acyl;

$R^2$ is hydroxy or acyloxy;

$R^3$ is hydrogen or hydroxy;

$R^4$ is hydrogen or hydroxy;

$R^5$ is hydrogen or hydroxysulfonyloxy; and $R^6$ is hydrogen or carbamoyl or a salt thereof.

11. The process of claim 9, wherein said cyclic peptide has the formula (II):

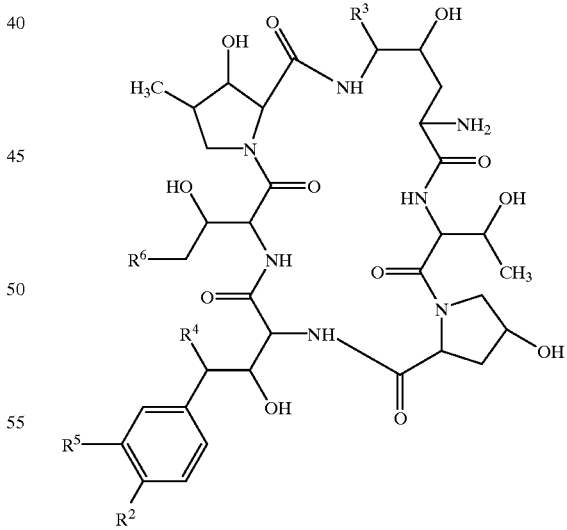

(II)

wherein $R^1$ is acyl;

$R^2$ is hydroxy or acyloxy;

$R^3$ is hydrogen or hydroxy;

$R^4$ is hydrogen or hydroxy;

$R^5$ is hydrogen or hydroxysulfonyloxy; and $R^6$ is hydrogen or carbamoyl or a salt thereof.

12. The process of claim 9, wherein said cyclic lipopeptide compound is selected from the group consisting of FR901379, Echinocandin B, and Aculeacin A.

13. The process of claim 9, wherein said acylase catalyzes deacylation of the acyl group $R^1$ of a cyclic lipopeptide compound of the following general formula (I):

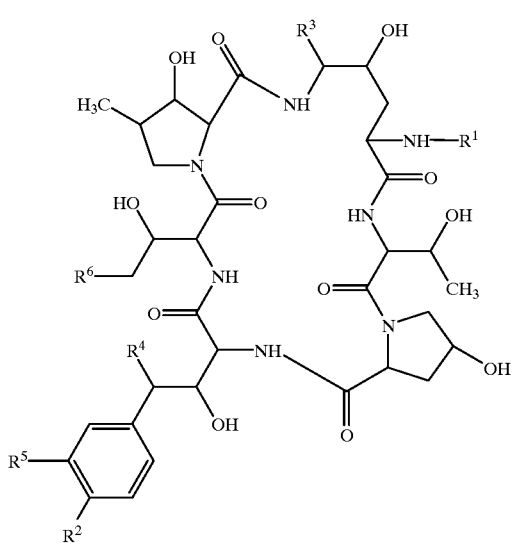

(I)

wherein $R^1$ is acyl;
$R^2$ is hydroxy or acyloxy;
$R^3$ is hydrogen or hydroxy;
$R^4$ is hydrogen or hydroxy;
$R^5$ is hydrogen or hydroxysulfonyloxy; and
$R^6$ is hydrogen or carbamoyl or a salt thereof, to give a cyclic peptide of the following general formula (II):

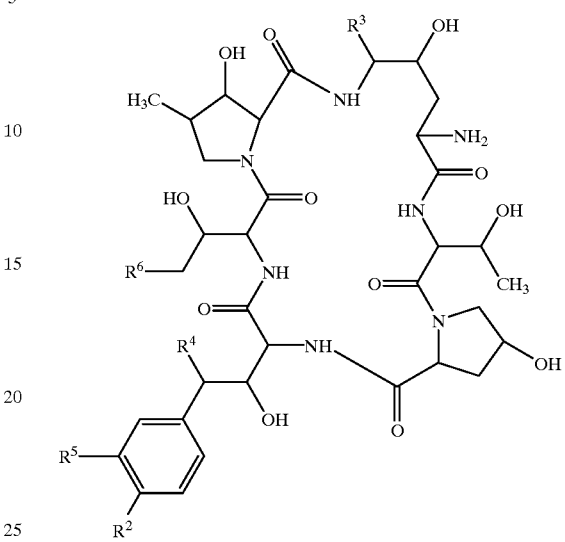

(II)

wherein $R^2$, $R^3$, $R^4$, $R^5$, and $R^6$ are the same groups as respectively defined above or a salt thereof; wherein the optimum pH for deacylation is from 3 to 5; the optimum temperature for deacylation is from 25 to 50° C.

14. A method of making the isolated acylase of clam 1, comprising culturing the strain Verticillium sp No. 30085 for a time and under conditions for the expression of an cyclic lipopeptide acylase;

isolating said cyclic lipopeptide acylase as a crude or purified enzyme solution.

* * * * *